US009241831B2

(12) United States Patent
Peartree et al.

(10) Patent No.: US 9,241,831 B2
(45) Date of Patent: Jan. 26, 2016

(54) REDUCTION OF INTRAOCULAR PRESSURE IN THE EYE USING A TUBULAR CLIP

(71) Applicant: IRIDEX Corporation, Mountain View, CA (US)

(72) Inventors: Kenneth A. Peartree, Danville, CA (US); Tim Buckley, Alamo, CA (US); Aaron Feustel, Claremont, NH (US)

(73) Assignee: IRIDEX Corporation, Mountain View, CA (US)

( * ) Notice: Subject to any disclaimer, the term of this patent is extended or adjusted under 35 U.S.C. 154(b) by 319 days.

(21) Appl. No.: 13/766,431

(22) Filed: Feb. 13, 2013

(65) Prior Publication Data

US 2014/0052046 A1    Feb. 20, 2014

Related U.S. Application Data

(60) Provisional application No. 61/598,208, filed on Feb. 13, 2012.

(51) Int. Cl.
*A61F 9/00* (2006.01)
*A61F 9/007* (2006.01)
*A61M 27/00* (2006.01)

(52) U.S. Cl.
CPC ............ *A61F 9/00781* (2013.01); *A61M 27/00* (2013.01)

(58) Field of Classification Search
CPC .......................... A61F 9/00781; A61M 27/00
See application file for complete search history.

(56) References Cited

U.S. PATENT DOCUMENTS

| 5,232,440 | A | 8/1993 | Wilk |
| 5,445,167 | A | 8/1995 | Yoon et al. |
| 5,968,058 | A | 10/1999 | Richter et al. |
| 6,203,513 | B1 * | 3/2001 | Yaron et al. ...................... 604/9 |
| 7,431,709 | B2 | 10/2008 | Pinchuk et al. |
| 7,850,637 | B2 | 12/2010 | Lynch et al. |
| 2004/0068252 | A1 | 4/2004 | Whitmore et al. |
| 2004/0210181 | A1 | 10/2004 | Vass et al. |
| 2004/0260227 | A1 | 12/2004 | Lisk, Jr. et al. |
| 2008/0103510 | A1 | 5/2008 | Taylor et al. |
| 2010/0274259 | A1 | 10/2010 | Yaron et al. |
| 2013/0168432 | A1 | 7/2013 | Vold et al. |

FOREIGN PATENT DOCUMENTS

WO    2011/116228 A2    9/2011

OTHER PUBLICATIONS

International Search Report and Written Opinion of International Application No. PCT/US2013/025868, mailed Apr. 15, 2013, 11 pages.

\* cited by examiner

*Primary Examiner* — Philip R Wiest
*Assistant Examiner* — Benjamin Klein
(74) *Attorney, Agent, or Firm* — Kilpatrick Townsend and Stockton LLP

(57) ABSTRACT

Drainage of aqueous from the anterior chamber of the eye can be facilitated by a malleable hollow clip or staple that can be formed to attach to ophthalmic tissue and provide intra-luminal flow of aqueous through the clip. In addition, the clip can be adjusted to modulate the outflow rate of aqueous, both during the initial surgical procedure as well as on a post-procedure basis. Furthermore, an instrument is described in which the forceps of the clip delivery device reside inside the lumen of hollow clip during deployment and manipulation. Features of an instrument are designed to secure the clip to the delivery forceps and prevent tissue blockage of the clip lumens. The clips may be color-matched to the underlying tissue for the purpose of camouflage and may carry pharmaceuticals.

19 Claims, 14 Drawing Sheets

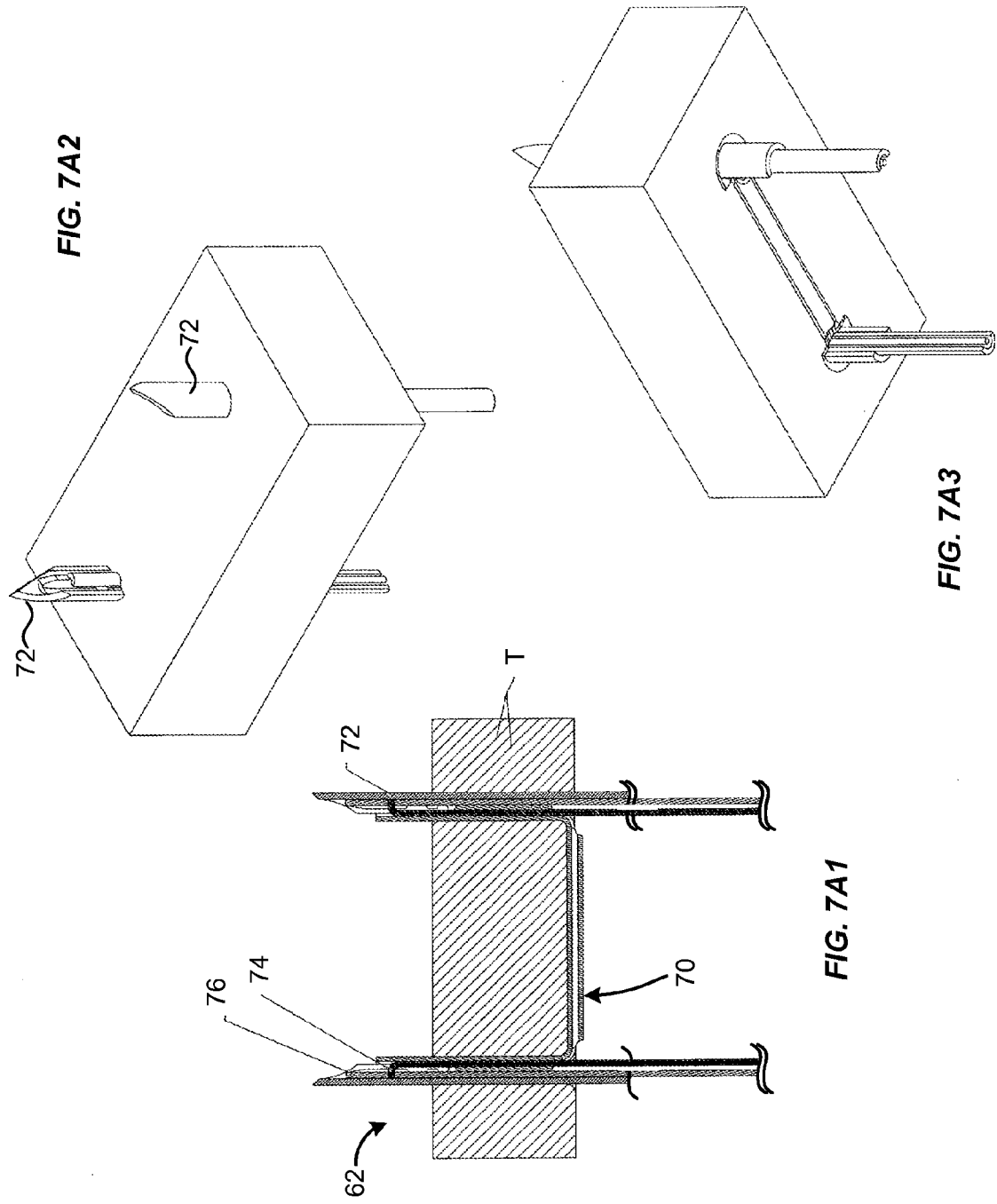

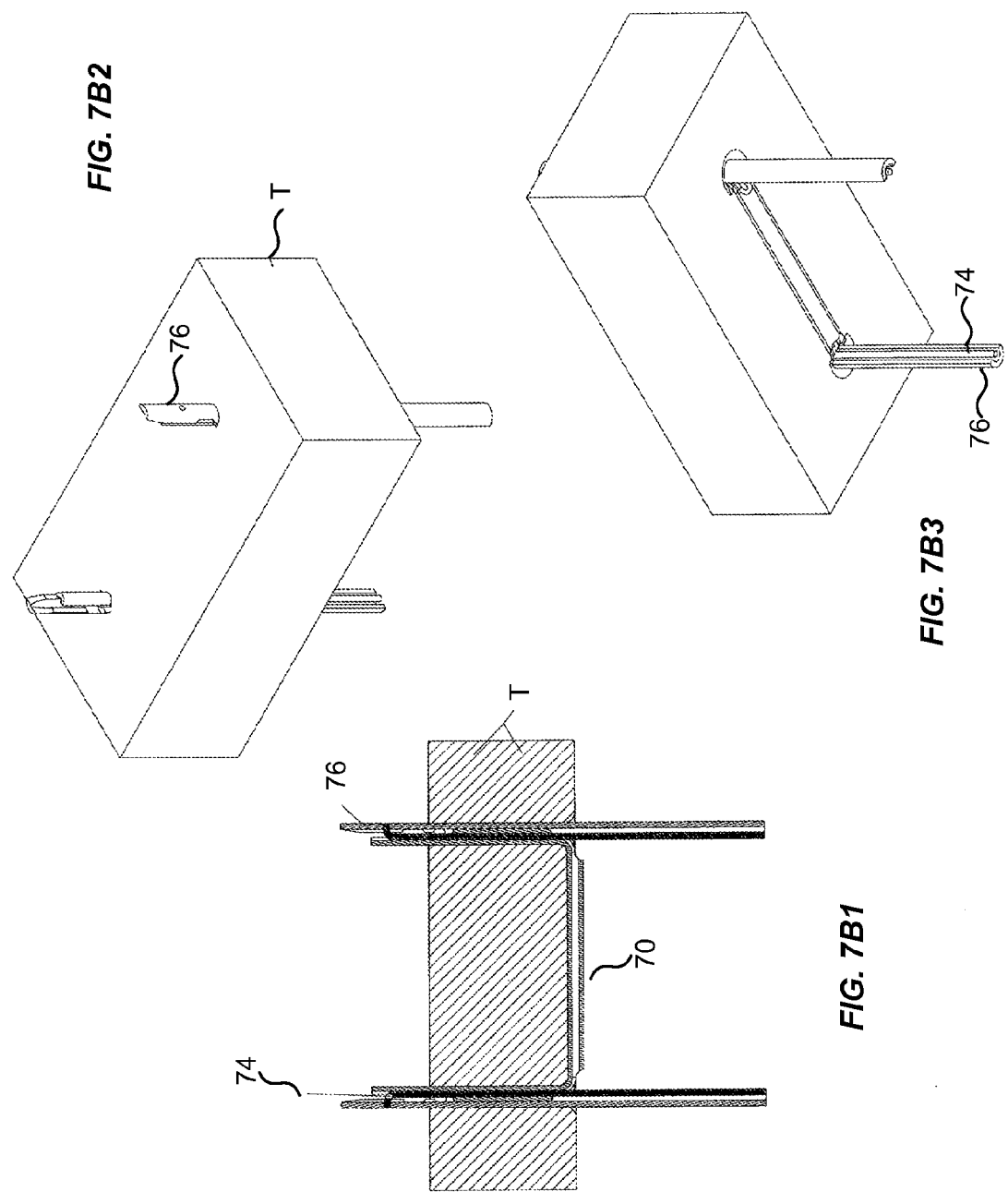

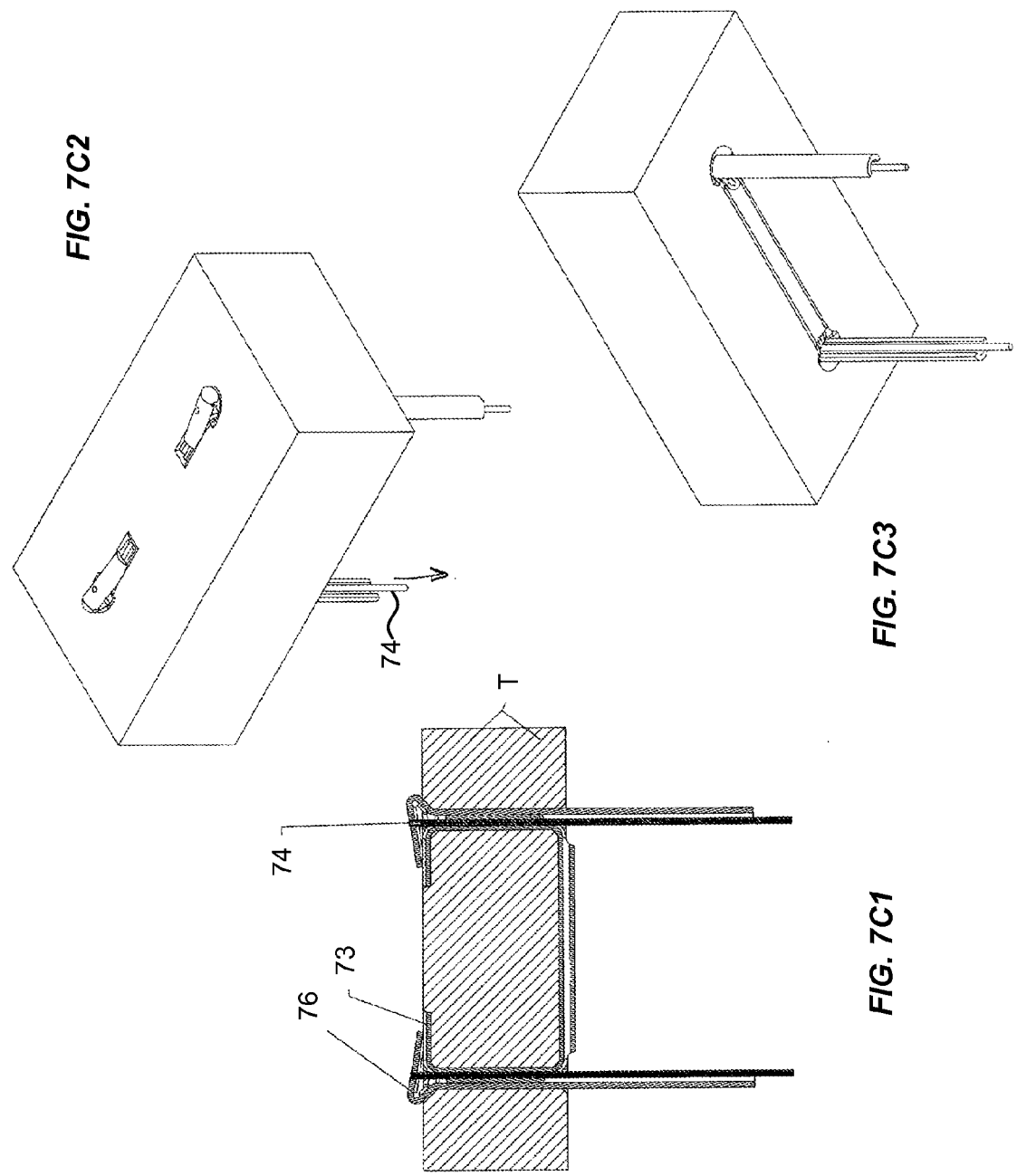

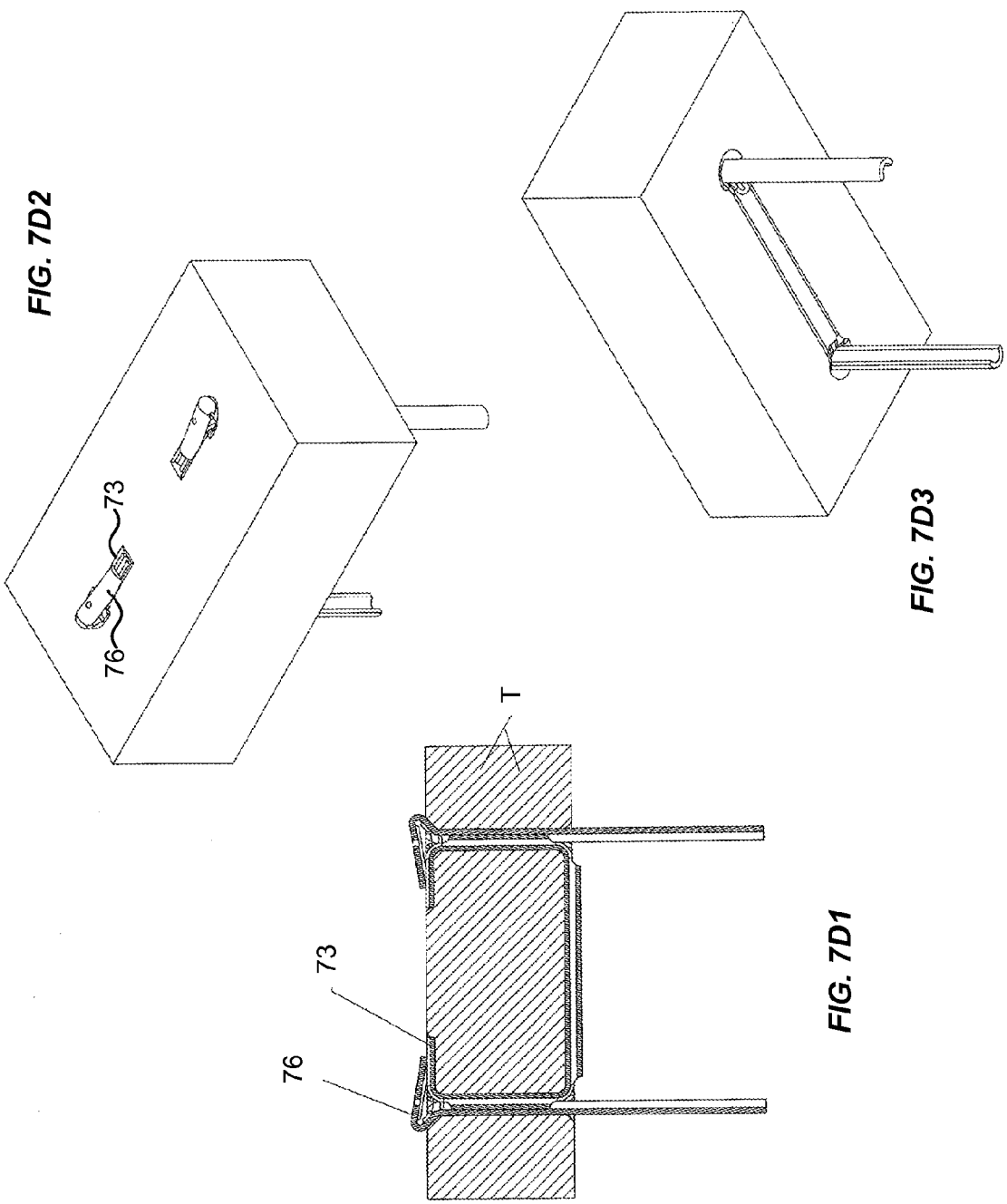

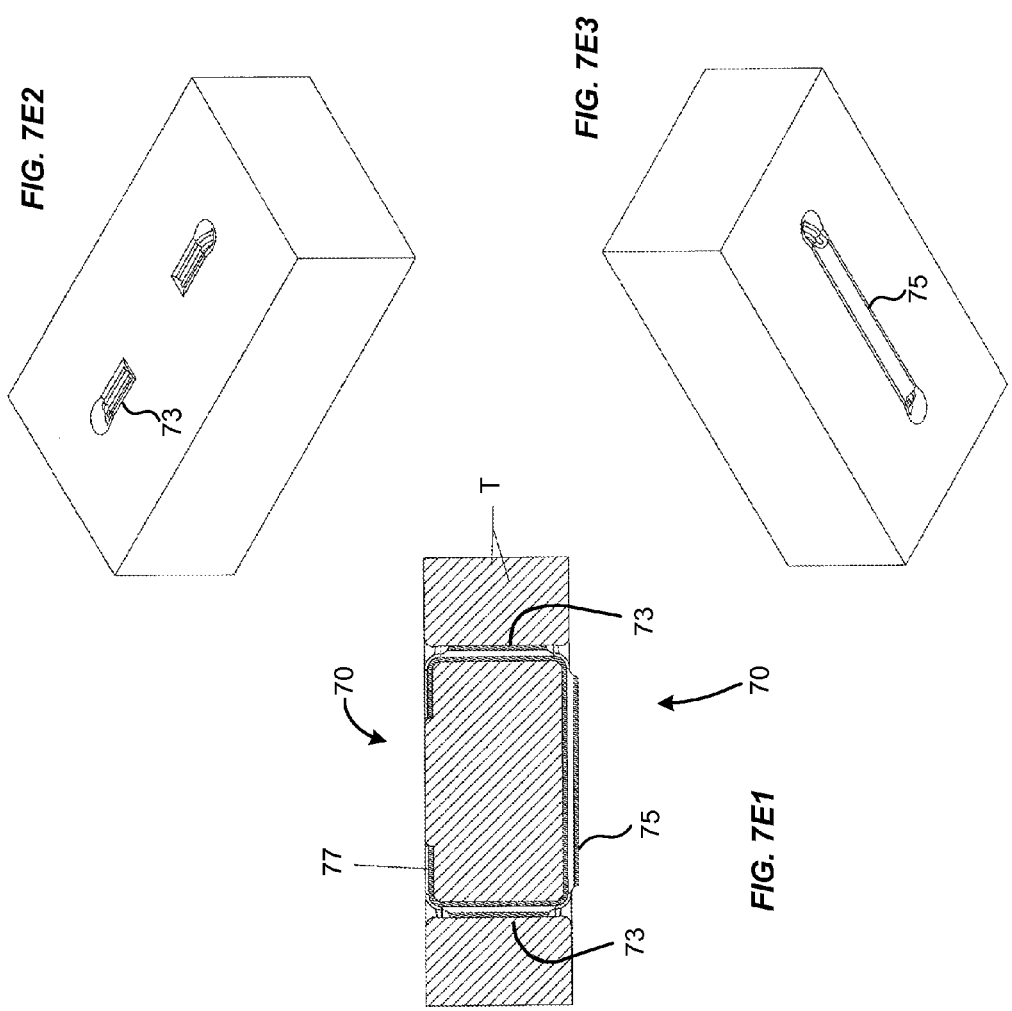

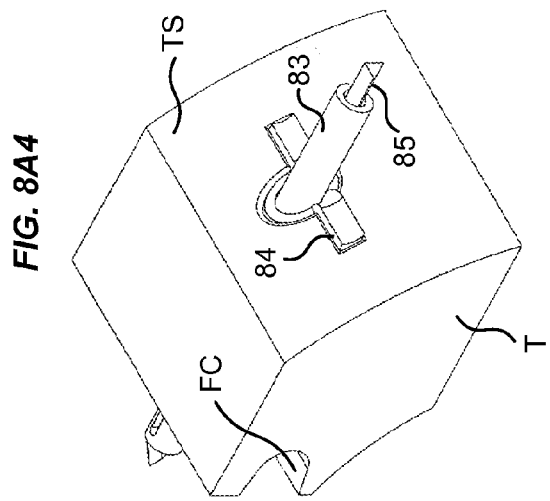
FIG. 8A4
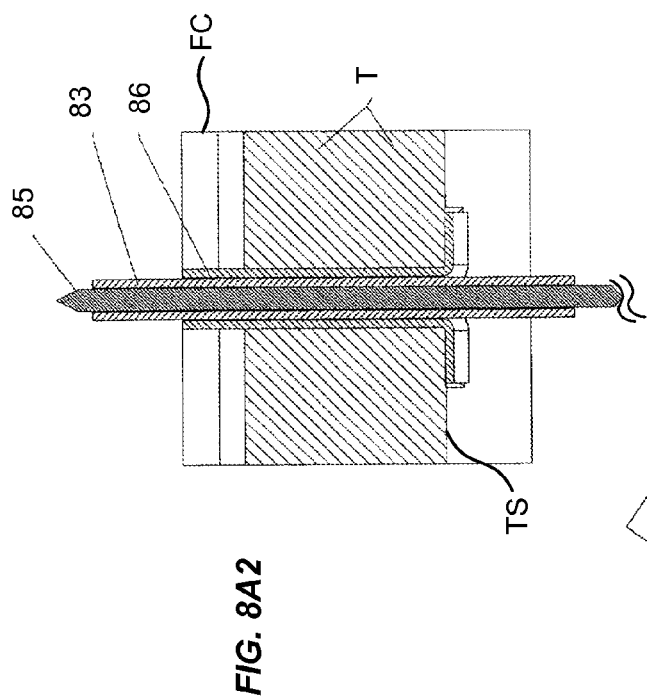
FIG. 8A2
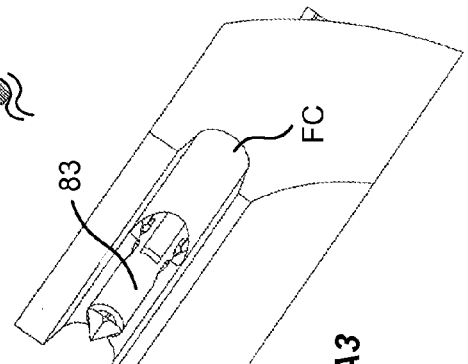
FIG. 8A3
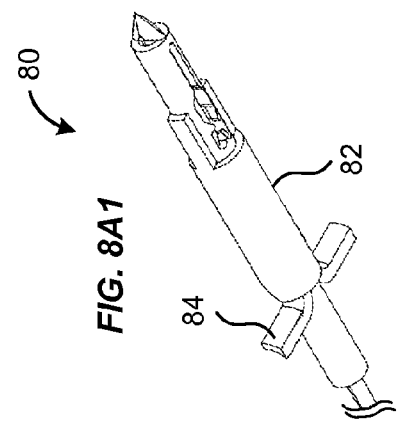
FIG. 8A1

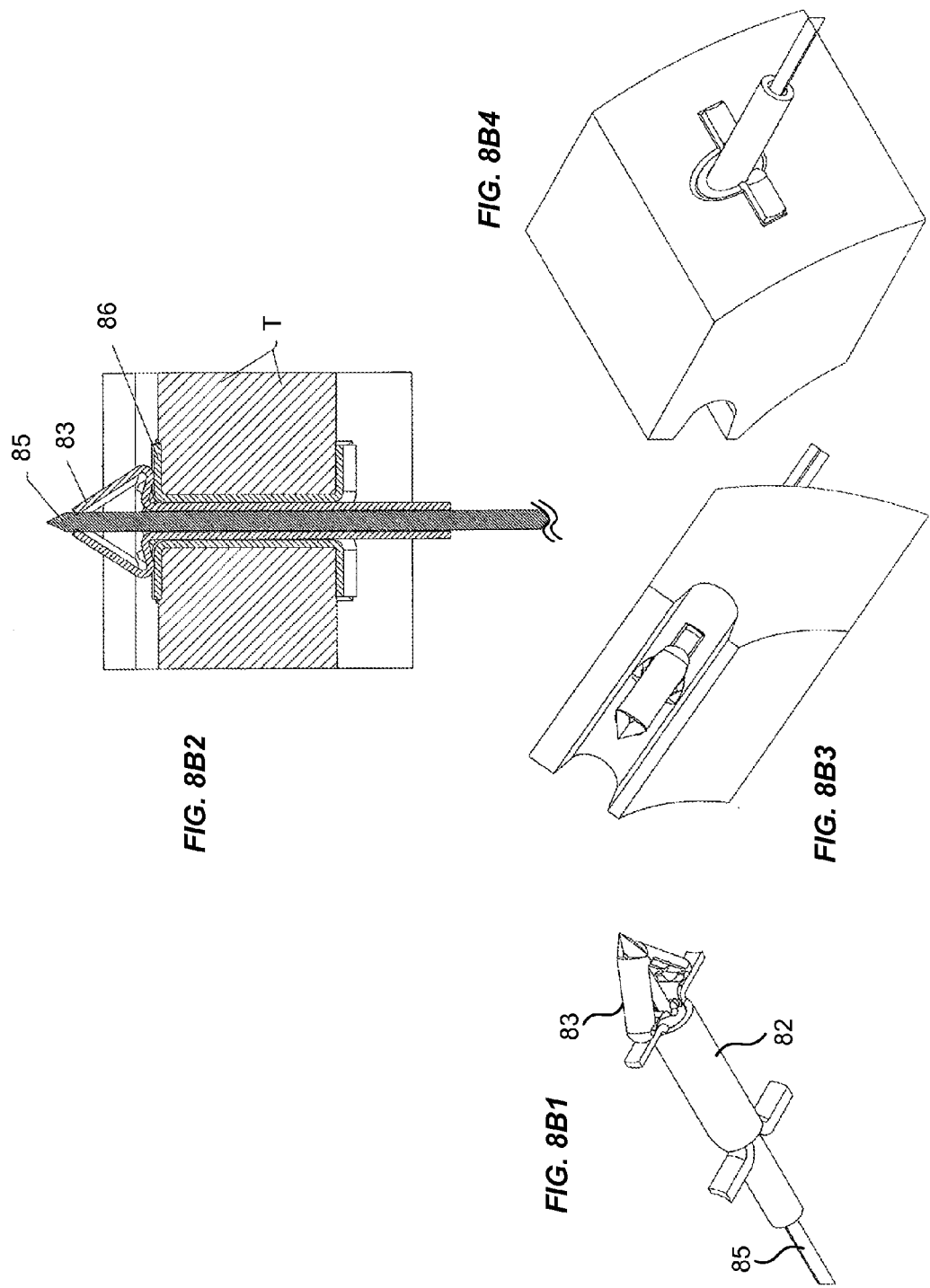

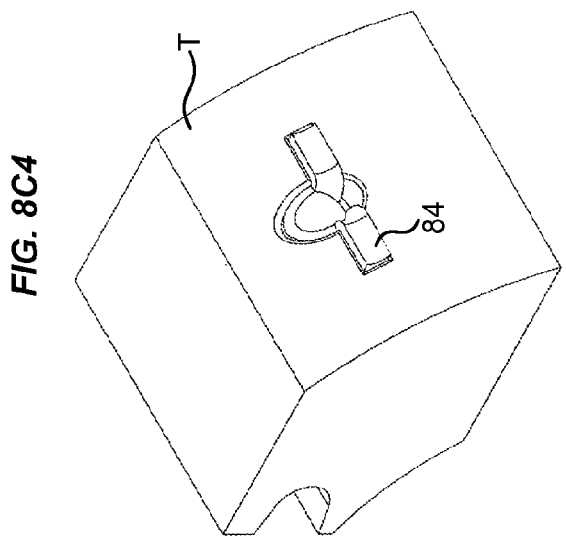
FIG. 8C4
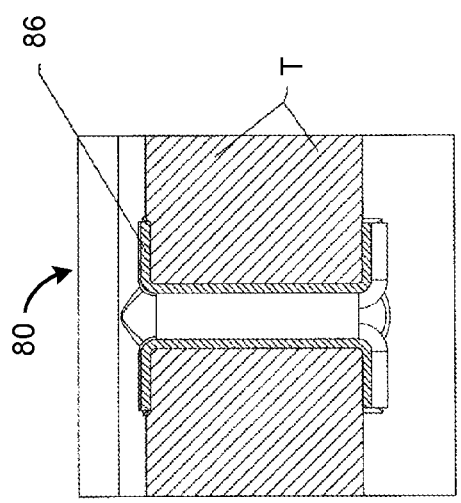
FIG. 8C2
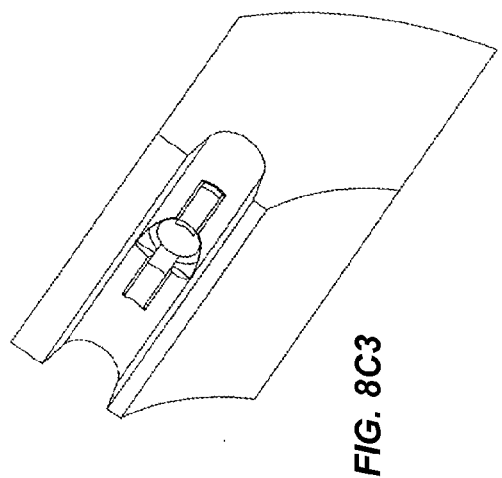
FIG. 8C3
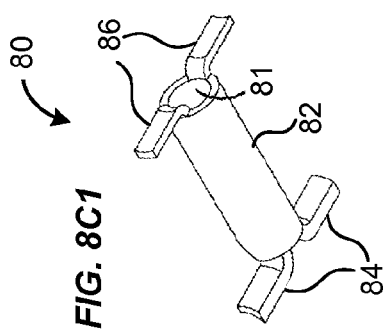
FIG. 8C1

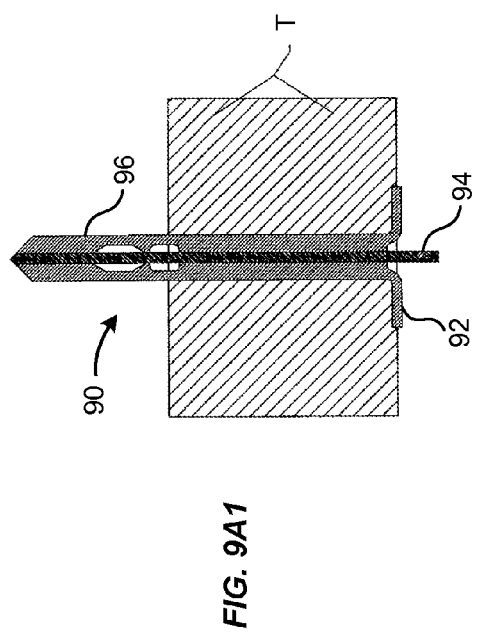
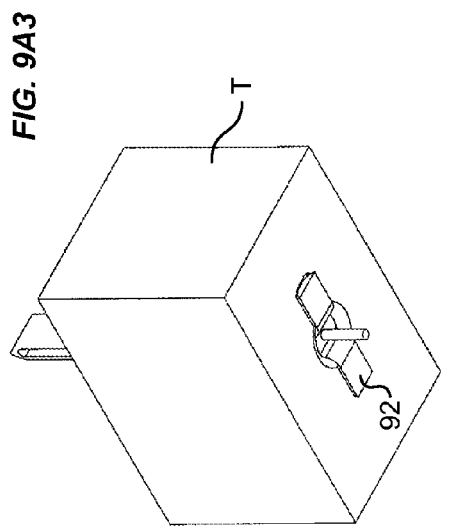
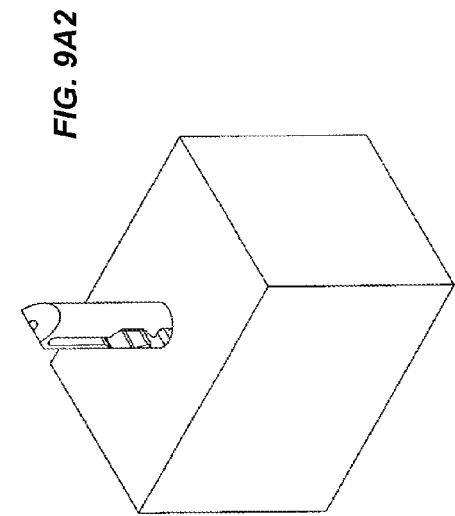
FIG. 9A1
FIG. 9A2
FIG. 9A3

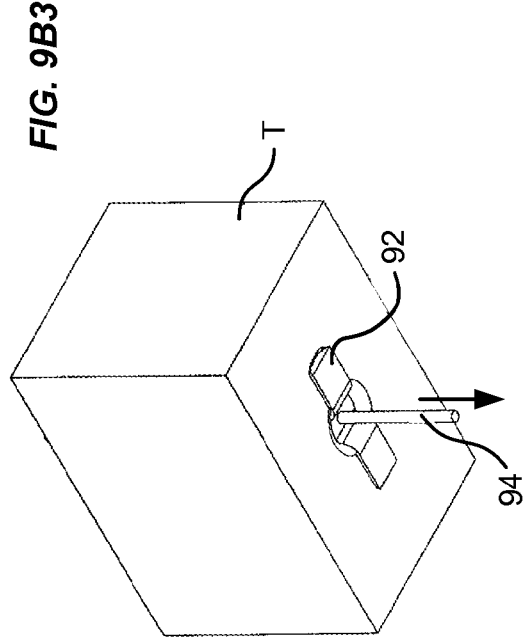
FIG. 9B3
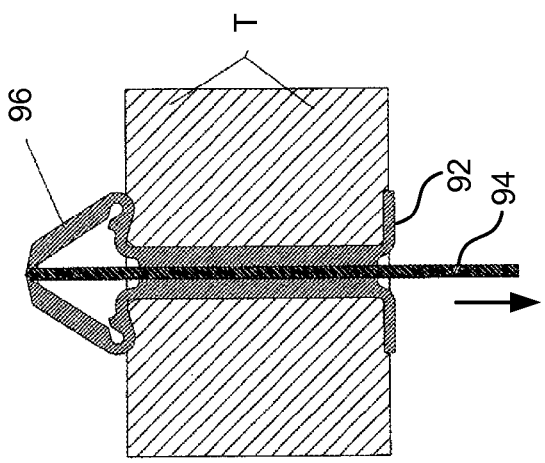
FIG. 9B1
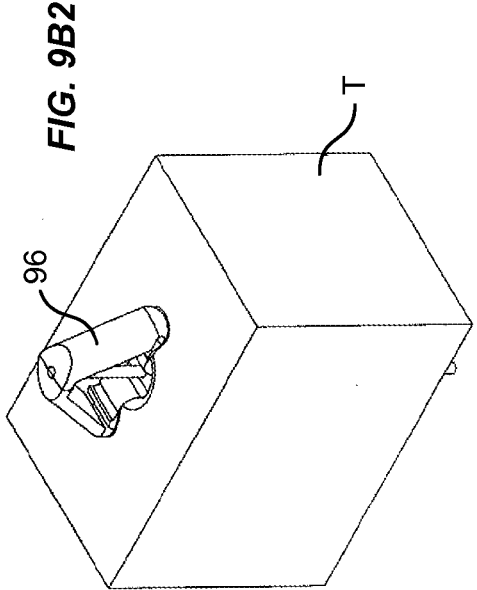
FIG. 9B2

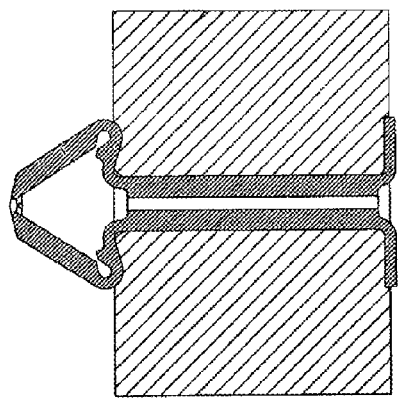
FIG. 9C1
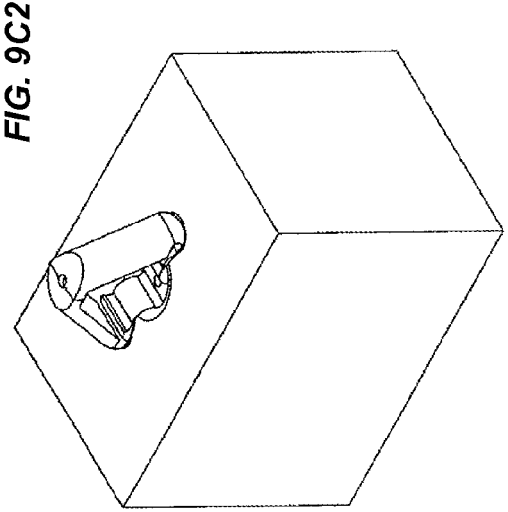
FIG. 9C2
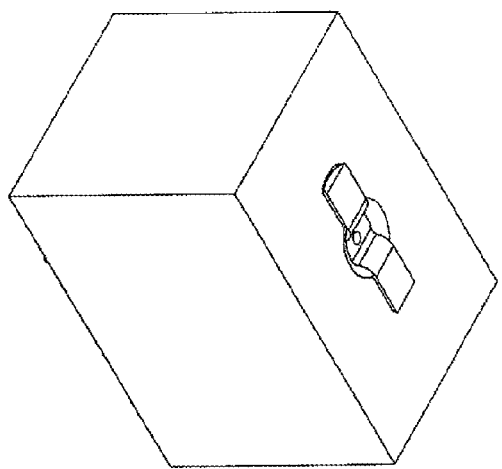
FIG. 9C3

REDUCTION OF INTRAOCULAR PRESSURE IN THE EYE USING A TUBULAR CLIP

CROSS-REFERENCES TO RELATED APPLICATIONS

The present application claims the benefit under 35 USC 119(e) of US Provisional Application No. 61/598,208 filed Feb. 13, 2012; the full disclosure of which is incorporated herein by reference in its entirety.

The subject matter of the present application is related to that of U.S. Non-Provisional Application No. 13/709,375 filed Dec. 10, 2012; the full disclosure of which is incorporated herein by reference in its entirety.

BACKGROUND OF THE INVENTION

1. Field of the Invention

The present invention relates generally to ophthalmic surgery. Exemplary embodiments relate to the treatment of glaucoma and other conditions by enabling drainage of aqueous fluid from the anterior chamber of the eye.

Glaucoma is one of the leading causes of blindness. It is caused by an increase in intraocular pressure (IOP), which can damage the optic nerve. The source of the increase in pressure is an imbalance in the production and drainage of the aqueous humor. Aqueous humor (aqueous) is the clear fluid that fills the front of the eye (anterior chamber) and is constantly being produced by the eye. Drainage of the aqueous occurs through the front of the eye in an area called the anterior chamber angle. In a normal eye, the rate of drainage is closely matched to the rate of production, thus maintaining healthy pressure in the eye. When the drainage of aqueous is impeded, IOP is increased.

For surgical treatment of glaucoma, a traditional surgical procedure such as trabeculectomy removes tissue in the anterior chamber angle, which creates an opening to facilitate drainage of the aqueous fluid and thus a reduction in IOP. The surgeon then creates a flap of sclera tissue above the angle opening to allow the fluid to drain through the scleral flap and into a reservoir space between the conjuctiva and the sclera. This reservoir of aqueous is called a bleb. One issue with the traditional trabeculectomy is that the opening created at the angle can become blocked or may close, which reduces or eliminates its effectiveness. To address this shortcoming, drainage devices exist to provide more predictable and lasting aqueous drainage. The present invention provides a novel method and exemplary embodiments of devices and system for fast, simple, and lasting aqueous drainage.

BRIEF SUMMARY OF THE INVENTION

The present invention generally provides improved medical devices, systems, and/or methods. Embodiments of the invention are particularly well suited for ophthalmic surgeries, including novel methods and devices to facilitate drainage of aqueous from the anterior chamber of the eye. One exemplary method involves utilization of a malleable hollow clip or staple that can be configured to attach to ophthalmic tissue and provide intra-luminal flow of aqueous through the clip. In addition, the clip can optionally be adjusted to modulate the outflow rate of aqueous, in some cases both during the initial surgical procedure as well as on a post-procedure basis. Furthermore, an instrument is described in which arms of forceps or other structure of a clip delivery device removably reside inside a drainage lumen of the hollow clip. Features of the instrument are designed to secure the clip to the delivery device, flush-mount the clip to tissue, and prevent tissue blockage of the clip lumens. A surface of the clips may be color-matched to the underlying tissue for the purpose of camouflage and/or may carry pharmaceuticals.

In one aspect, the invention provides a method for draining excess fluid from a region of a patient body, the region bordered by a tissue. The method comprises penetrating the tissue so as to advance an elongate leg of drain clip distally into the tissue. The tissue is engaged with a base of the drain clip, and at least a portion of the leg of the advanced drain clip is deformed so that so that the base and the leg affix the drain clip to the tissue. The excess fluid can be passed from the region along a channel of the leg.

In another aspect, the invention provides a system for draining excess fluid from a region of a patient body, the region bordered by a tissue. The system comprises a draining clip having an elongate leg configured for advancing distally into the tissue. The leg has a channel extending along it, and the draining clip also includes a base disposed adjacent a proximal end of the leg. The base can be oriented to engage the tissue, optionally to help halt advancement when the clip has been advanced to a desired depth. At least a portion of the leg of the advanced drain clip is configured to be deformed so that the base and the leg affix the drain clip to the tissue, and so as to pass the excess fluid from the region along the channel of the leg.

In some embodiments, the region of the body that will be drained may comprise a volume of an eye of the patient. The tissue may comprise a tissue of the eye, and the passing of the fluid along the channel may help mitigate excess intra ocular pressure (IOP) of the eye, including IOP related to glaucoma. The channel of the leg may optionally have an inner diameter of about 0.002"- 0.008" and the leg may have an outer diameter of about 0.005"-0.013". In some embodiments, the channel may have (or may have receive) a material therein which helps provide a desired flow rate. A selectable number of legs may be provided to provide an associated selectable flow rate.

The leg will often comprise a tubular body having a proximal opening and a distal opening with a lumen therebetween so as to serve as the channel. The leg may be configured to be advanced distally with a deployment shaft disposed in the lumen so as to inhibit ingress of tissue therein. The shaft may be withdrawn proximally from the lumen so as to facilitate passing the fluid along the lumen. Optionally, the shaft can be included in a deployment assembly that releasably supports the clip while penetrating the tissue. The deployment assembly may, in some embodiments, include a sharpened distal end extending distally of the draining clip so as to facilitate the penetrating of the tissue, with the sharpened distal end optionally being disposed on the shaft in the lumen, a body or shaft that extends outside and alongside the leg, or the like. Some embodiments of the deployment assembly may comprise an actuatable shaft extending along the leg, and deforming of the leg may be induced from outside the tissue by actuating the actuatable shaft so that the shaft induces bending of a distal foot of the leg laterally to capture the tissue between the foot and the base. The actuatable shaft can comprise a wire or shaft extending distally within the leg to a deformation mechanism and/or body, wherein a proximal movement of the shaft pushes the deformation mechanism and/or body laterally against the foot so as to deform the foot. In some embodiments the deformation mechanism and/or body may be a structure disposed inside the leg. In other embodiments, a deformation mechanism may be incorporated into the foot, so that the load on from the shaft bears on and induces bending of the foot. When the deformation body is included in the deployment assembly, the deformation body may be configured so that pulling the deformation body proximally through the draining clip straightens the deformation body and leaves the draining clip in the tissue when the deployment assembly is withdrawn from the patient.

In many embodiments, a plurality of legs of a draining clip system will be advanced into the tissue. Optionally, the base may span between first and a second legs of a single clip. In other embodiments, the base may comprise tubular material extending from a proximal end of a tubular leg, with the base being formed by splitting the tube locally and splaying portions of the tube outward in opposed directions.

BRIEF DESCRIPTION OF THE DRAWINGS

FIGS. 7A1-7A3 (collectively "FIG. 7A") illustrate an embodiment of a draining clip with 2 legs connected by a spanning linkage in its first stage of deployment, with its piercing-support mechanism and deployment mechanism puncturing a layer of tissue so that the span is flush with the tissue.

FIGS. 7B1-7B3 illustrate the same embodiment as FIG. 7A in a second stage of deployment when the piercing-support mechanism has been withdrawn from the tissue.

FIGS. 7C1-7C3 illustrates the same embodiment as FIG. 7A in a third stage of deployment when the deployment mechanism bends the end of each leg over to form a closed draining clip.

FIGS. 7D1-7D3 illustrate the same embodiment as FIG. 7A in a fourth stage of deployment when the actuation wires are withdrawn from the tissue.

FIGS. 7E1-7E3 illustrate the same embodiment as FIG. 7A in a fifth and final stage of deployment when the remainder of the deployment mechanism is withdrawn from the tissue.

FIGS. 8A1-8A4 illustrate an embodiment of a draining clip with at least one leg ending in a splayed 'T' on one end in a first stage of deployment with its piercing-deployment mechanism puncturing a layer of tissue so that the splayed 'T' is flush with the tissue.

FIGS. 8B1-8A4 illustrate the same embodiment as FIG. 8A in a second stage of deployment when the actuation linkage has been pulled back so that the other end of the leg has been splayed open in a 'T' so that it is flush with the tissue.

FIGS. 8C1-8C4 illustrate the same embodiment as FIG. 8A in a third stage of deployment when the actuation linkage has been released so that the actuation mechanism can be withdrawn through the middle of the draining clip.

FIGS. 9A1-9A3 illustrate an embodiment of a draining clip with at least one leg ending in a splayed 'T' on one end in the first stage of deployment with its piercing-deployment actuator puncturing a layer of tissue so that the splayed 'T' is flush with the tissue.

FIGS. 9B1-9B3 illustrate the same embodiment as FIG. 9A in a second stage of deployment when the piercing-deploying actuator has been pulled back so that the other end of the leg has been splayed open in a triangular shape which is flush with the tissue.

FIGS. 9C1-9C3 illustrate the same embodiment as FIG. 9A in a third stage of deployment when the piercing-deploying actuator has been withdrawn through the clip.

DETAILED DESCRIPTION OF THE INVENTION

Figure 1:
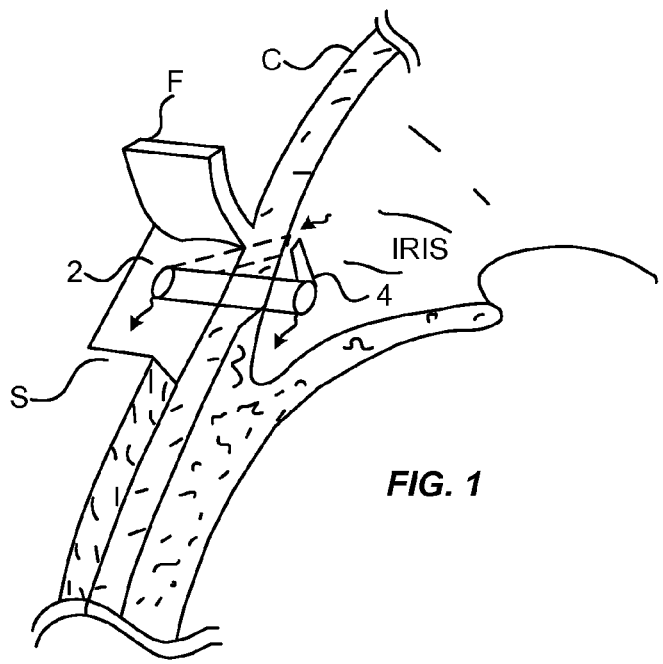
FIG. 1 illustrates an exemplary method of using a clip underneath a scleral flap to facilitate aqueous drainage.

Methods and devices are provided for the drainage of aqueous humor and the reduction of IOP. FIG. 1 illustrates an exemplary method of utilizing a hollow and malleable clip 2, or staple, that can be affixed to a layer of tissue such as the sclera S and provide a pathway for drainage through that tissue. One or both of the clip's legs 4 are hollow and perform the dual function of affixing to the tissue (when formed closed by a pair of compatible forceps) and allowing intra-luminal flow of fluid. FIG. 1 illustrates one exemplary method of placing a clip to facilitate a trabeculectomy wherein the clip is formed or bent from a pre-insertion configuration to a closed configuration and thereby affixed to a layer of tissue, so that the clip provides drainage of aqueous from the anterior chamber of the eye to an area underneath a scleral flap F. Flap F may be affixed over the top of the deployed clip outside cornea C as will be understood by those of skill in the art.

Figure 2:
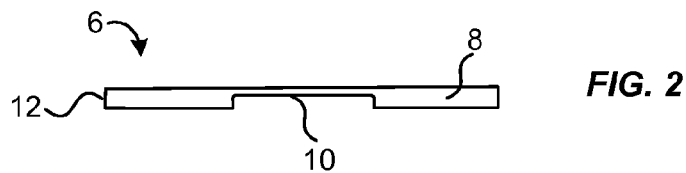
FIG. 2 illustrates an exemplary embodiment of the apparatus wherein the clip is manufactured from a single tube.

FIG. 2 illustrates an exemplary embodiment of a clip apparatus 6 that can be made from a tube of any biocompatible malleable material such as tantalum, stainless steel, titanium, and/or plastic. More specifically, a desired length of the tube material 8 can be provided, with localized area(s) routed, cut, or skived using any number of methods such as machine tools, laser energy, or chemical etching. Using such methods, features can be cut in the tube in any desired number of locations to facilitate inflow and outflow of fluid. In this particular embodiment shown, a portion 10 of the tube is routed to provide an area of outflow and the tube ends 12 are utilized for inflow, with the routed portion optionally forming a base of the clip between two tubular legs, and the lumens of the legs facilitating fluid drainage through a tissue in which the clip will be deployed.

Figure 3:
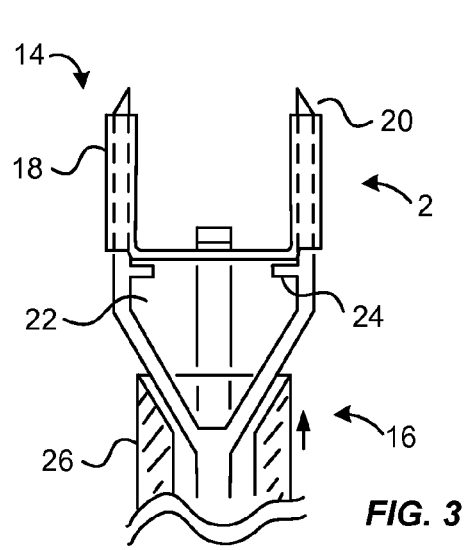
FIG. 3 illustrates an exemplary embodiment of a delivery forceps apparatus carrying a hollow clip.

FIG. 3 schematically illustrates an exemplary embodiment of a clip deployment system 14, including clip 2 mounted to a forceps apparatus 16 that can be used in the placement and fixation of the clip in tissue. In this embodiment, the tubular legs 18 of the clip 2 are each loaded over the ends of the forceps 16 such that the tips of the forceps jaws 20 extend just past the ends of the clip legs. The forcept tips 20 may be sharpened so as to penetrate sclera S. This apparatus provides a number of clinical advantages. First, with the tubular legs of the clip loaded directly over the forceps, the clip is securely held (such as by a spring-loaded tab 22) such that it can be prevented from inadvertently falling off of the forceps. Moreover, having the clip loaded on the forceps in this manner provides good control of the formation of the clip during fixation in tissue. A second clinical advantage to the embodiment shown is that the sharpened forceps tips do the work of penetrating the tissue and blocking the lumens of the hollow clip in order to prevent unwanted ingress of tissue that could block and otherwise impair drainage through the clip.

In operation of the embodiment shown in FIG. 3, a handle provides for axial movement of outer shaft 26. When the handle pushes the outer shaft forward, it compresses the forceps jaws and thus the closes the attached malleable clip, and thus fixating it in the tissue. Features on the forceps are shown that are intended to prevent the clip from sliding backward during insertion of the forceps and clip into tissue. These physical stops on the forceps jaws also assist in the flush mounting of the clip against the tissue surface prior to closing of the jaws. An additional feature shown in this embodiment is the spring-loaded tab 22 that can provide the dual function of a physical stop to prevent the clip from sliding forward off the forceps jaws and as an anvil that helps shape the clip during formation when the jaws are closed. To release the clip from the jaws when deployment is complete, the spring-loaded tab can be moved out of the way by action of the handle.

Figure 4:
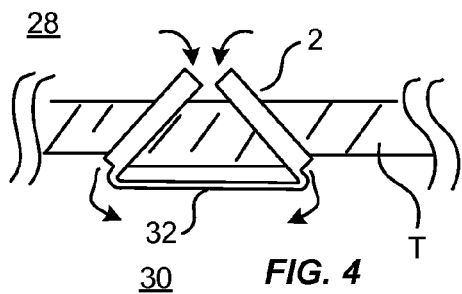
FIG. 4 illustrates an exemplary embodiment of a formed, implanted clip through tissue to facilitate aqueous drainage.

FIG. 4 illustrates an exemplary embodiment of a closed clip 2 wherein the forceps jaws have formed the clip into a triangular shape that fixates the clip to the tissue T and resists further movement. However, the hollow clip leg ends remain exposed to the fluid for the purpose of a desired drainage flow of fluid through tissue T from a high-pressure region 28 to a lower pressure region 30. Outflow of the fluid occurs at the proximal end of the clip legs, on the opposite side of the tissue layer from the cantilevered distal ends, where the clip has been cut to form base 32 and permit such drainage. In other embodiments, flow may be permitted from the proximal end toward the distal ends.

There may be circumstances in which it is desirable to remove or reposition the clip after insertion and/or implantation. This could be performed with the same forceps used to deploy the clip, or may be performed by specialty forceps optimized for clip removal. Forceps jaws can re-acquire the lumens of the clip legs in a manner similar to FIG. 3 such that the forceps jaws slide into the hollow clip legs. Due to the malleable nature of the clip material, the forceps jaws can be actuated to move outward and thus open the clip legs to a position roughly perpendicular to the tissue to facilitate withdrawal of the clip. At that point, the clip could either be removal or re-deployed in another position.

The present invention includes a method for adjustable flow rate of fluid through the clip. This is optionally achieved by changing the geometry and/or size of either the in-flow or out flow orifices on the clip. This can be accomplished by using the malleable nature of the clip material to pinch the lumen(s) or otherwise modify the shape of the clip to alter the cross-sectional area of a clip orifice. Alternatively, inserts could be placed into and/or removed from the lumens. Moreover, adjustments to the clip flow rate could be made either during the initial surgical procedure or on a post-procedure basis to adjust fluid flow without necessitating removal of the clip.

Figure 5:
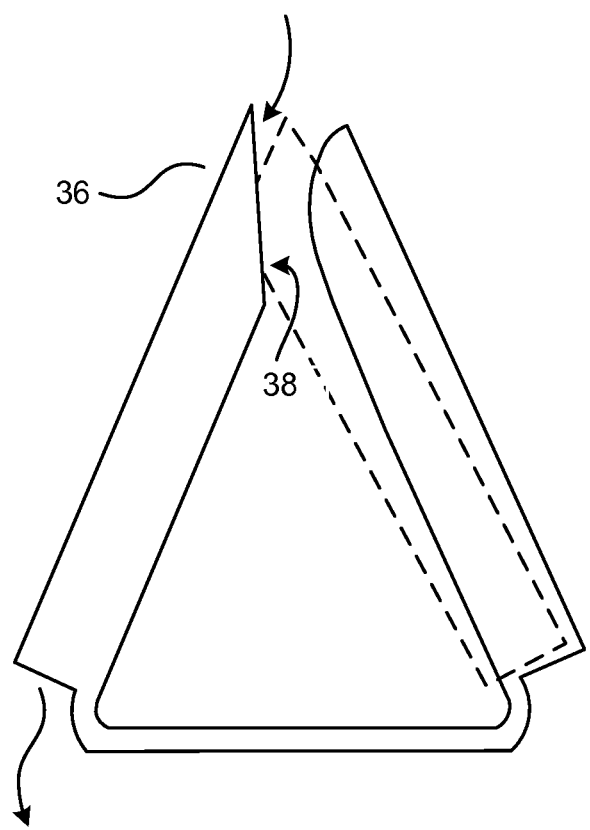
FIG. 5 illustrates an exemplary embodiment of an apparatus for the hollow clip that can provide for adjustable flow of aqueous fluid.

FIG. 5 illustrates an exemplary embodiment of a clip apparatus that can adjust the drainage rate. The embodiment is similar to those shown in FIGS. 1-4. However, in this embodiment, one arm of the clip has a leg 36 with an open lumen 38 whereas the other leg 40 of the clip is closed and rounded. To alter the effective open cross-sectional area of lumen 38 exposed to fluid (and thus adjusting the flow rate), the legs are pushed toward each other such that the closed and rounded end of one clip leg can partially or completely abut the open-ended lumen, and/or away from each other so as to increase the flow. The proximity of the closed-ended clip leg next to the open lumen clip leg increases or decreases the exposed surface area of the open lumen and adjusts the flow rate.

In a method related to adjustment of the clip flow rate, the handle and forceps used to deploy the clip can be calibrated to communicate clip orifice size and/or flow rate to the operator. A given position of the handle imparts a position to the forceps jaws and thus a relative forming position of the clip. In the embodiment illustrated in FIG. 5, for example, the handle can be calibrated to indicate the relative proximity of the clip legs (and therefore orifice size). Thus, for a given position of the handle, the size of clip orifice can be known and calibrated to handle position. Therefore, appropriate markings can be made to the handle to indicate orifice size and/or clip flow rate. This can be conducted either during the initial surgical procedure or on a post-procedural basis to adjust the clip flow rate to meet patient needs.

Figure 6:
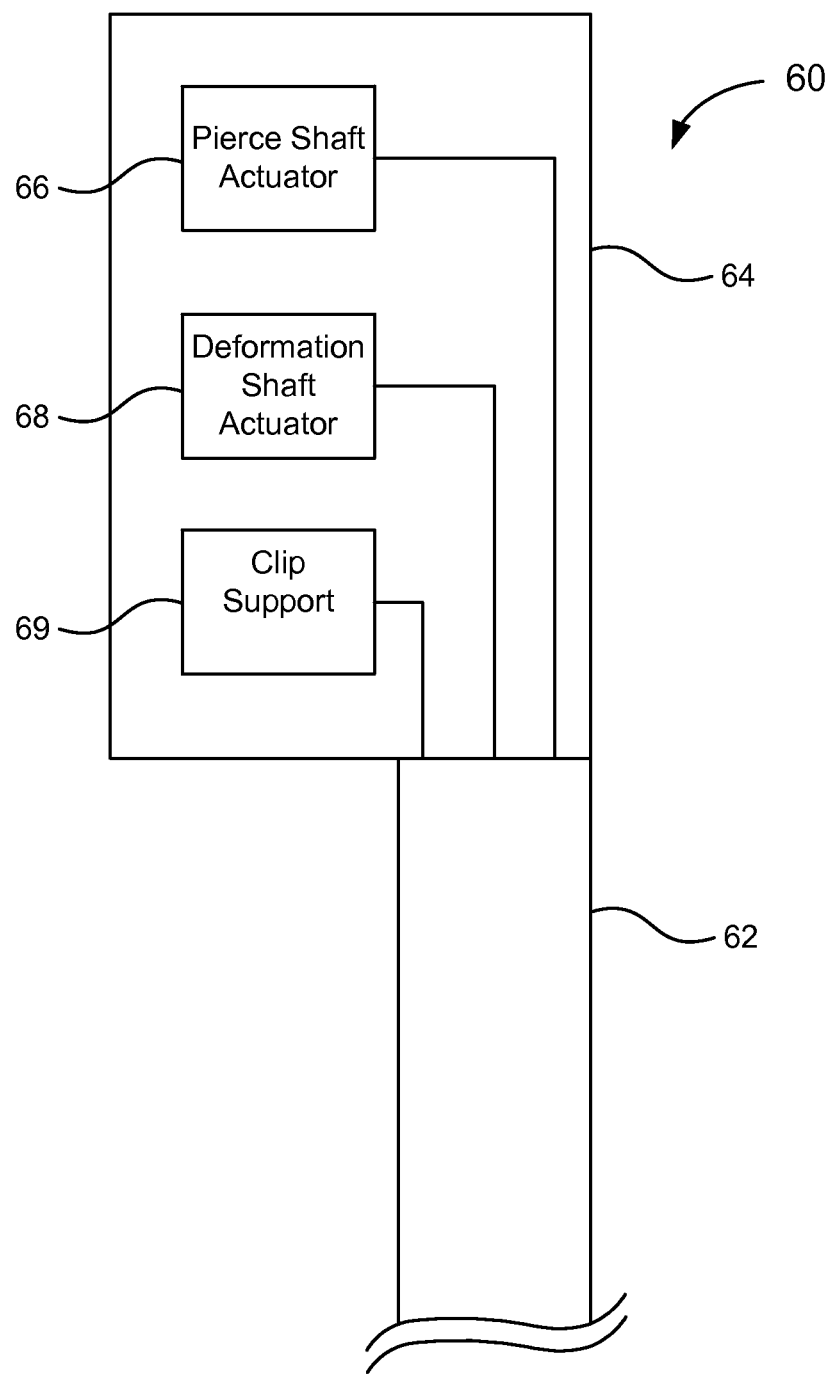
FIG. 6 schematically illustrates a handle and proximal end of a shaft for use in deploying embodiments of the clips described herein.

Referring now to FIG. 6, exemplary embodiments of the draining clip and associated deployment device of at least FIGS. 7A-7E (and optionally other embodiments described herein) may include a handle 60 coupled to a proximal end of a deployment shaft assembly 62 so as to support and selectively articulate clip deployment structures disposed adjacent a distal end of the deployment assembly. More specifically, the deployment system may include handle 60, with the handle having a handle body 64 that optionally supports a pierce shaft actuator mechanism 66 which releasably holds a piercing-support mechanism in place while it is piercing the tissue, and which can be actuated from adjacent the handle so as to withdraw the piercing-support mechanism or shaft from the tissue. Additionally, handle 60 includes a deformation shaft actuator mechanism 68 supported by handle body 64 which allows the operator to articulate a deformation mechanism, such as by pulling on actuation wires or an actuation shaft to deform the clip. In some embodiments, additional actuation of the deformation mechanism (or another structure) may facilitate release of the clip from the deployment system, such as by further pulling an action wire or shaft until they break away from the rest of the distal deployment mechanism and are free to be withdrawn from the draining clip. A clip support structure 69 attached to the handle body 64 holds the clip (and optionally additional components of the distal deployment mechanism) in place with relation to the handle body during at least a portion of the deployment, and can also (for example) prevent the draining clip from moving relative to the deployment mechanism (and/or other deployment structures) until the deployment mechanism has been fully actuated and the actuation wires have been withdrawn.

Referring now to FIGS. 7A-7C, the distal portion of deployment assembly 62 is shown in more detail. A clip 70 is releasable supported adjacent a distal end of deployment assembly 62, and the deployment assembly can help to both insert the clip into a tissue T and deploy the clip so that the clip is affixed to the tissue and the deployment assembly can be withdrawn. A pair of piercing-supports 72 of deployment assembly 62 have sharp distal tips which help to pierce tissue T, typically so that the tissue can be affixed to the clip and/or so that the tissue can be retained by the clip. Piercing-support 72 may comprise a rigid structure having a channel which supports and protects the deployment mechanism and clip from the tissue during this piercing action. A pair of actuation wires 74 are affixed to a deployment body or mechanism 76, and are configured to cause deployment body or mechanism 76 to be displaced and/or deformed when the deployment wires are pulled. Further pulling or proximal displacement of the actuation wires 74 proximally relative to the deployment body or mechanism 76 may then separate the wires from the deployment mechanism (via a frangible weld, bond, or other detachable interface between the wires and foot, via a frangible distal portion of the wires formed by notching or otherwise weakening the wire locally, or the like). The wires can thus be withdraw from the clip and tissue when the deployment mechanism has bent the legs of the clip.

The structure and deformation of clip 70 may be seen in FIGS. 7C and 7E. Clip 70 generally includes first and second tubular legs 73 with a body 75 extending therebetween. At least a portion of legs 73 are deformable so that at least a displaceable portion or foot 77 of each leg moves relative to body 75 so as to affix the clip to tissue T. Note that in some embodiments the displaceable portion or foot 77 may encompass most or all of the leg. Note also that the legs may be plastically and/or resiliently deformable, and that the body may or may not be tubular as can be understood from the various embodiments described herein.

Deformation of clip 70 and removal of the wires 74 can be understood with reference to FIGS. 7C and 7D. To deploy the clip, deployment mechanism 76 is configured to deform in multiple locations under the column and/or bending load imposed by wires 74 in order to bend the legs 73 of the draining clip 70. The exemplary draining clip 70 has two hollow legs 73 connected by a span or base 75, and portions near both ends of both legs have been narrowed or relieved so that they may be bent over more easily than the rest of the legs. Both ends of one or both legs may also optionally provide direct access to the lumen or hollow center of the legs. Once deployed, this optionally allows fluid to pass through one or both legs so as to alleviate overpressure or the like. The intra-leg lumen(s) may also allow the actuation wires to pass through. Actuation of deployment mechanism 76 by pulling of wires 74 initially displaces deployment mechanism or body 76 and that body bends, deforms, and displaces foot 77 of each leg 73 relative to the base of the clip. Further actuation then separates the wires from the deployment body from the distal end of the deployment assembly, and may also pull the wires from the clip.

The deployed clip after removal of the deployment assembly can be seen most clearly in FIG. 7E, with the clip and tissue being shown in cross-section if FIG. 7E1, the distal portion of the deployed legs (and a distal tissue surface) shown in FIG. 7E2, and the clip body 75 and proximal tissue surface seen in FIG. 7E3. The clip in the embodiment of FIG. 7 can be configured to allow aqueous humor to drain through the sclera tissue and/or other tissues of the eye (referred to as tissue or material) which legs 73 penetrates and capture. Alternative embodiments may allow other fluids to draft though any material that might be penetrated by legs 73, captured, and thereby allowing structures or hollow bodies to be drained. In this embodiment, the clip can be oriented so that the handle is on the exterior of the eye and the deployment side or distal ends of legs 73 of clip 70 are in the anterior chamber of the eye. This and or other embodiments may also be used to adjoin tissue planes or layers, to adjoin angled or abutted tissue edges, planes, or both, and/or to adjoin more than 2 tissues, or may be used to merely reinforce a single piece of tissue. The clip might also be used to adjoin other materials besides tissue, or any combination thereof. While this embodiment shows a pair of legs connected by a single span, the same concept could be used with one or more legs connected in a linear or non-linear string or matrix pattern by zero or more spans. Hence, total drainage properties through a tissue may be selected by deploying a desired number and/or array of clips. The actuation mechanism and handle assembly might also carry more than one draining clip in a magazine or clip. The actuation and handle assembly might deploy more than one draining clip in more than one location at once. The tip of the clip might be split into multiple toes which might be folded over by the actuation mechanism in one or more directions.

Embodiments of the device such as those of FIG. 7 which focus on ophthalmic applications may be quite small, optionally having a clip leg lumen ID of about 0.002"-0.008", a leg OD of about 0.005"-0.013", a span of the device between the legs of less than 0.3" (ideally being about 0.080"), and/or a penetration depth of less than 0.2" (such as about 0.040"). Other applications may employ clips and devices with different sizes. Note that some or all of the legs of a clip may be partially or fully blocked, plugged, or solid (such as by using other deployment mechanisms) and this may be different for each leg. While this embodiment is intended for ophthalmic applications and so might have a clip which is made of a deformable and biocompatible material such as stainless steel, titanium, tantalum, platinum, and/or gold, this or other applications could use a wide variety of other clip materials.

A method for deploying the embodiment of FIG. 7 (and a variety of other related embodiments) may comprise one or more elements from the following steps:

1. Press the distal end of the deployment assembly and clip distally against the surface of the tissue or other material to be secured until the material has been fully penetrated by the piercing-support mechanism and the body or span of the clip is flush with the material, as shown in FIG. 7A.
2. With the clip flush against the material, actuate the pierce shaft actuator 66 of the device which withdraws the piercing-supporting mechanism from the material, as shown in FIG. 7B.
3. With the clip still flush against the material, actuate the deformation shaft actuator 68 so as to pull wires 74 proximally and articulate the deployment mechanism or foot 76 to bend the end of each leg 73 which is the second action in the device, as shown in FIG. 7C.
4. While maintaining pressure against the clip with the device, actuate the third action in the device which withdraws the actuation wires 74 proximally from the clip, as shown in FIG. 7D.
5. Pull the deployment assembly away from the material, which will straighten the deployment mechanism or foot 76 and pull it out of the lumen of the clip leg 73 and material or tissue T, leaving the clip in the material, as shown in FIG. 7E.

Referring now to FIGS. 8A1-8C4, another exemplary embodiment of a draining clip 80 is shown with adjacent components of the delivery system but without tissue in FIG. 8A1 (prior to deployment) and FIG. 8B1 (during deployment), and the clip is shown after deployment and removal of the deployment system in FIG. 8C1. Interactions between clip 80 and tissue T can be understood with reference to FIGS. 8A2-8A4; 8B2-8B4, and 8C2-8C4.

Draining clip 80 generally includes a tubular leg 82 having a proximal base 84, with a portion of the leg comprising a foot 86 that is displaceable relative to the base so as to affix the clip within tissue T. Leg 82 often includes a lumen 81 so as to provide drainage therethrough and the associated deployment device of FIGS. 8A-8C includes a handle 60 (see FIG. 6) with a deformation actuation mechanism within the handle 68. This allows the operator to pull proximally on a shaft of the actuation linkage until a tissue piercing distal end of a tissue pierce shaft 85 moves proximally so that the shaft expands a distal deployment mechanism 83, which in turn splays the end or foot 86 of the leg 83 into a 'T.' After actuation so as to deform the foot the deformation actuator may be configured to allow the actuation linkage to return distally to its pre-deployment position. Distal movement of shaft 85 allows the actuation mechanism 83 to return to its smaller cross-section pre-deployment shape, allowing the shaft and deployment mechanism to be withdrawn proximally through the lumen of the deployed leg. A clip support structure 69 attached to the handle (see FIG. 6) holds the rest of the deployment mechanism with relation to the handle and prevents the draining clip from moving along deployment mechanism towards the handle until the deployment mechanism has been withdrawn from the clip.

In this embodiment, the pierce shaft actuator may be omitted and/or incorporated into the deformation actuator, and the shaft 85 of the actuation linkage has a sharp tip to pierce tissue as well as causing the deployment mechanism to deform when it is pulled. Deployment mechanism 83 articulates, bends, and/or deforms in multiple desired locations under the column load imposed by shaft 85 in order to bend the leg 82 (and specifically the feet 86) of the draining clip with a desired deformation, and the deployment mechanism is configured to also collapse back toward its pre-deployment small profile shape when pulled through the draining clip.

Draining clip 80 may comprise a single hollow leg with both ends relieved so that they may be bent over more easily than the rest of the leg, and with one end (typically the proximal end) of said leg typically being pre-bent into a 'T' shape, and with both ends of the leg providing direct access to lumen 81 or the hollow center of said leg for the actuation mechanism to pass through during deployment, and for fluid to pass through after deployment.

The clip in this embodiment may be configured to allow aqueous humor to drain through the sclera tissue through which it penetrates and captures, though any material might be penetrated, captured, and drained. In this embodiment, the clip can be oriented so that the handle is on the exterior of the eye and the deployment side of the clip is advanced from an anterior chamber of the eye into tissue of the eye, including tissues along the fluid outflow pathways of the eye. For example, as shown in FIGS. 8A2-8A4, clip 80 and the associated distal end of the deployment assembly can be advanced distally into a tissue surface TS exposed to fluids of the anterior chamber of the eye during an intra-ocular procedure. The sharpened tip of shaft 85 and foot 86 may be advanced through a tissue of the eye near the angle of the eye (formed by the iris and cornea as seen in FIG. 1), and/or to or from a natural or artificial fluid outflow pathway channel FC, so that the foot can be deformed in or adjacent the angle or channel and the open ends of the clip leg are affixed exposed to the channel and the anterior chamber so as to provide fluid flow.

While this embodiment is not shown adjoining tissue planes, the same (or similar) embodiment could be effectively used to adjoin diagonal tissue edges, tissue planes, or both, and may adjoin more than 2 tissues, or may be used to merely reinforce a single piece of tissue. The clip might also be used to adjoin other materials besides tissue, or any combination thereof. While this embodiment shows a single leg not connected by any span to additional legs, the same concept could be used with multiple legs connected in a linear or non-linear string or matrix pattern by one or more spans. The actuation mechanism and handle assembly might also carry more than one draining clip in a magazine or clip. The actuation and handle assembly might deploy more than one draining clip in more than one location at once. One or each tip of the clip might be split into only one, two, three, or more than 3 toes or feet which could be pre-folded on the proximal or handle side of the clip and might be folded over by the actuation mechanism in one or more directions on the distal or far side of the clip. Exemplary embodiments of the device focuses on ophthalmic applications (and thus the clip leg ID may be in a range of about 0.002"-0.008", the leg OD may be about 0.005"-0.013", and the axial length of the leg proximal of the foot may optionally be configured for a penetration depth of about, very roughly 0.040"), other applications may employ clips and devices with different sizes. Note that some or all of the leg of a clip may be partially or fully blocked, plugged, or in the case of using other deployment mechanisms, may be solid, and this may be different for each clip used in a clip system. While this embodiment is intended for ophthalmic applications and might have a clip which is made of a deformable and biocompatible material such as stainless steel, titanium, tantalum, platinum, or gold, this or other applications could use other clip materials.

A method for using the embodiment of FIGS. 8A-C may optionally entail one or more of the following steps:

1. Press the device assembly distally against a surface of the material to be secured until the material has been fully penetrated by the piercing-deployment mechanism and clip and the proximal, pre-splayed 'T' is flush with the material, as shown in FIG. 8A2-8A4.
2. With the proximal, pre-splayed proximal 'T' of the clip flush against the material, actuate the device so that the piercing-deployment mechanism splays open the other, distal end of the clip, as shown in FIG. 8B.
3. De-actuate the deployment device and pull it away from the material and clip. This will straighten the piercing-deployment mechanism and pull it out of the clip, leaving the clip in the material, as shown in FIG. 8C.

Referring now to FIGS. 9A1-9C3, another exemplary embodiment of the draining clip 90 includes a hollow leg having a proximal end with a base 92 in the form of a pre-splayed "T" similar to that described above. Rather than having a removable deployment mechanism deform a foot of the leg, the foot has a structure which can be actuated and remain with the deployed clip. More specifically, draining clip 90 is included in a deployment system having a handle (see FIG. 6) that includes an actuation mechanism which allows the operator to pull on a piercing-deploying actuator shaft until the shaft fully deploys a foot 96, after which the shaft breaks away from the deployed foot 96 or tip of the draining clip 90 and is withdrawn through the clip. A support structure such as a shaft attached to the handle (not shown) can hold the draining clip 90 fixed with relation to the handle until the piercing-deploying actuator 94 is withdrawn through the clip. Piercing-deploying actuator 94 causes foot 96 the draining clip 90 to deform when it is pulled, and more specifically to extend laterally from the leg of the clip so as to affix the clip to tissue T.

Draining clip 90 may be formed from a single hollow tube with a proximal end locally weakened or relieved so that it may be bent over more easily than the rest into a 'T' shape. The other end or distal end may be locally weakened so as to deform in multiple locations under a column load imposed by the actuator 94 in order to acquire a triangular shape, the base of which becomes flush with the tissue. Both ends of the leg may again provide direct access to the hollow center of said leg for drainage and/or for the piercing-deploying actuator to pass through.

Clip 90 and similar embodiments may be designed to allow aqueous humor to drain through the sclera tissue (referred to as tissue or material) which it penetrates and captures, though any material might be penetrated, captured, and drained. In this and related embodiments, clip 90 can be oriented so that the handle is on the exterior of the eye and the deployment side of the clip is in the anterior chamber of the eye. While this embodiment is not shown adjoining tissue planes, the same (and/or similar) embodiment could be effectively used to adjoin diagonal tissue edges, tissue planes, or both, and may adjoin more than 2 tissues, or may be used to merely reinforce a single piece of tissue. The clip might also be used to adjoin other materials besides tissue, or any combination thereof. While this embodiment shows a single leg not connected by any span to additional legs, the same concept could be used with multiple legs connected in a linear or non-linear string or matrix pattern by one or more spans. The actuation mechanism and handle assembly might also carry more than one draining clip in a magazine or clip. The actuation and handle assembly might deploy more than one draining clip in more than one location at once. Each tip of the clip might be split into only one, two, three, or more than 3 toes which would be prefolded on the handle side of the clip and might be deformed into a multi-sided pyramid in one or more directions on the far side of the clip.

While clip 90 is well suited for ophthalmic applications (optionally with the clip ID being 0.002"-0.008", OD bing 0.005"-0.013", and/or the leg configured for a penetration depth of less than 0.3, such as about 0.040"), other applications may employ clips and devices with different sizes. Note that some or all of the legs of a clip may be partially or fully blocked, plugged, or in the case of using other deployment mechanisms, may be solid, and this may be different for each leg. While this embodiment is intended for ophthalmic applications and so might have a clip which is made of a deformable and biocompatible material such as stainless steel, titanium, tantalum, platinum, or gold, this or other applications could use other clip materials.

A method for using clip 90 may optionally comprise one or more of the following steps:

1. Press the device assembly distally against the surface of the material to be secured until the material has been fully penetrated by the piercing-deployment actuator and by the leg of the clip, so that the splayed 'T' or other base is flush with the material, as shown in FIG. 9A.
2. With the splayed 'T' of the clip flush against the material, actuate the device so that the piercing-deployment actuator splays open the other end of the clip, as shown in FIG. 9B.
3. Continue to pull on the piercing-deployment actuator so that the actuator shaft is pulled through the clip, leaving the clip in the material, as shown in FIG. 9C.

For each method and apparatus described herein, the clips can incorporate surface modifications for further clinical benefit. One possible surface modification is to add color to at least a portion of a surface of the clip (such as the portion adjacent an exposed anterior surface of the eye) that would allow the clip to become camouflaged to the surrounding tissue for aesthetic purposes. For example, a clip could be made white in order to blend with sclera tissue. Another possible surface modification could be the addition of pharmaceuticals to meet a variety of clinical needs.

The embodiments discussed herein are illustrative. As these embodiments are described with reference to illustrations, various modifications or adaptations of the methods and/or specific structures described may become apparent to those skilled in the art.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A method for draining excess fluid from a region of a patient body, the region bordered by a tissue, the method comprising:
   penetrating the tissue so as to advance an elongate leg of a drain clip distally into the tissue;
   engaging the tissue with a base of the drain clip;
   deforming at least a portion of the leg of the advanced drain clip so that the base and the leg affix the drain clip to the tissue; and
   passing the excess fluid from the region along a channel of the leg;
   wherein the leg comprises a tubular body having a proximal opening and a distal opening with a lumen therebetween, the channel comprising the lumen, the leg being advanced distally with a deployment shaft disposed in the lumen so as to inhibit ingress of tissue therein; and
   wherein the shaft is withdrawn proximally from the lumen so as to facilitate passing the fluid along the lumen, the shaft being included in a deployment assembly that releasably supports the clip while penetrating the tissue, the deployment assembly including a sharpened distal end extending distally of the drain clip so as to facilitate the penetrating of the tissue, wherein the deployment assembly comprises an actuatable shaft extending along the leg, and wherein deforming of the leg is induced from outside the tissue by actuating the actuatable shaft so that the shaft bends a distal foot of the leg laterally to capture the tissue between the foot and the base.

2. The method of claim 1, wherein the region comprises a volume of an eye of the patient, wherein the tissue comprises a tissue of the eye, and wherein the passing of the fluid along the channel mitigates excess intra ocular pressure of the eye.

3. The method of claim 1, wherein the actuatable shaft comprises a wire or shaft extending distally within the leg to a deformation body, wherein a proximal movement of the shaft pushes the deformation body laterally against the foot so as to deform the foot.

4. The method of claim 3, wherein the deformation body is included in the deployment assembly, and further comprising pulling the deformation body proximally through the draining clip, the pulling of the deformation body straightening the deformation body so as to leave the draining clip in the tissue when the deployment assembly is withdrawn from the patient.

5. The method of claim 1, wherein a plurality of legs of a draining clip system are advanced into the tissue, and wherein the base spans between a first and a second leg.

6. The method of claim 5, further comprising deforming simultaneously at least two of the plurality of legs by actuating the actuatable shaft of the deployment assembly.

7. The method of claim 1, wherein the drain clip comprises a biocompatible malleable material selected from the group comprising tantalum, gold, platinum, titanium, stainless steel, or plastic.

8. The method of claim 1, wherein an exterior surface portion of the drain clip is colored to match the tissue.

9. The method of claim 1, further comprising eluting or administering pharmaceuticals with the drain clip.

10. A system for draining excess fluid from a region of a patient body, the region bordered by a tissue, the system comprising:
    a draining clip having:
        an elongate leg configured for advancing distally into the tissue, the leg having an channel extending thereal-ong; and
        a base disposed adjacent a proximal end of the leg, the base orientable to engage the tissue;
        wherein at least a portion of the leg of the advanced drain clip is deformable so that the base and the leg affix the drain clip to the tissue, and so as to pass the excess fluid from the region along the channel of the leg, the leg comprising a tubular body having a proximal opening and a distal opening with a lumen therebetween, the channel comprising the lumen, the leg being configured to be advanced distally with a deployment shaft of a deployment assembly disposed in the lumen so as to inhibit ingress of tissue therein; and wherein the shaft is configured to be withdrawn proximally from the lumen so as to facilitate passing the fluid along the lumen, the deployment assembly releasable supporting the clip and including a sharpened distal end extending distally of the drain clip so as to facilitate the tissue penetration, wherein the shaft of the deployment assembly comprises an actuatable shaft, wherein actuating the actuatable shaft from outside the tissue deforms of the leg so that the shaft bends a distal foot of the leg laterally to capture the tissue between the foot and the base.

11. The system of claim 10, the region comprising a volume of an eye of the patient, the tissue comprising a tissue of the eye, wherein the drain clip is configured to pass the fluid along the channel so as to mitigate excess intra ocular pressure of the eye, the channel of the leg having an inner diameter of about .002"-.008" and the leg having an outer diameter of about .005"-.013".

12. The system of claim 10, wherein the actuatable shaft comprises a wire or shaft extending distally within the lumen of the leg to a deformation body, wherein a proximal movement of the shaft pushes the deformation body laterally against the foot so as to deform the foot.

13. The system of claim 12, wherein the deformation body is included in the deployment assembly, and wherein the deformation body is configured to be pulled proximally through the draining clip so that the pulling of the deformation body straightens the deformation body so as to leave the draining clip in the tissue when the deployment assembly is withdrawn from the patient.

14. The system of claim 10, wherein the leg is included within a plurality of legs of the draining clip system, the legs configured to be advanced into the tissue so as to provide a plurality of parallel drainage paths, and wherein the base spans between first and a second leg of the plurality of legs.

15. The system of claim 14, wherein at least two of the plurality of legs are configured to be deformed simultaneously by actuating the actuatable shaft of the deployment assembly.

16. The system of claim 10, wherein the leg is configured to accommodate an adjustment to the channel after deployment so as to provide for adjustable flow rate of fluid through the deployed drainage clip.

17. The system of claim 10, wherein the drain clip comprises a biocompatible malleable material selected from the group comprising tantalum, gold, platinum, titanium, stainless steel, or plastic.

18. The system of claim 10, wherein an exterior surface portion of the drainclip is colored to match the tissue.

19. The system of claim 10, wherein the drain clip is further configured to elute or administer pharmaceuticals.

* * * * *